(12) United States Patent
Kendall et al.

(10) Patent No.: US 6,420,617 B1
(45) Date of Patent: *Jul. 16, 2002

(54) PROCESS FOR PRODUCING HEXABROMOCYCLODODECANE

(75) Inventors: John K. Kendall, Magnolia, AR (US); Jeffrey T. Aplin, Baton Rouge, LA (US)

(73) Assignee: Albemarle Corporation, Richmond, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/876,902

(22) Filed: Jun. 8, 2001

Related U.S. Application Data

(63) Continuation of application No. 09/373,639, filed on Aug. 18, 1999, now Pat. No. 6,284,935, which is a continuation-in-part of application No. 09/353,181, filed on Jul. 14, 1999, now abandoned, which is a continuation-in-part of application No. 09/253,874, filed on Feb. 22, 1999, now abandoned.

(51) Int. Cl.[7] .............................................. C07C 17/02
(52) U.S. Cl. ...................................................... 570/246
(58) Field of Search ................................ 570/234, 252, 570/247

(56) References Cited

U.S. PATENT DOCUMENTS

| | | |
|---|---|---|
| 3,544,641 A | 12/1970 | Versnel |
| 3,558,727 A | 1/1971 | Jenkner et al. |
| 3,652,688 A | 3/1972 | Olechowski et al. |
| 3,833,675 A | 9/1974 | Newcombe et al. |
| 4,301,058 A | 11/1981 | Neukirchen et al. |
| 4,530,880 A | 7/1985 | Taniuchi et al. |
| 4,783,563 A | 11/1988 | Taniuchi et al. |
| 4,849,134 A | 7/1989 | Georlette et al. |
| 4,918,253 A | 4/1990 | Hermolin et al. |
| 5,004,847 A | 4/1991 | Beaver et al. |
| 5,004,848 A | 4/1991 | Beaver et al. |
| 5,025,110 A | 6/1991 | Beaver |
| 5,043,492 A | 8/1991 | Ransford |
| 5,077,444 A | 12/1991 | Cook, Jr. et al. |
| 5,246,601 A | 9/1993 | Jensen |
| 5,292,450 A | 3/1994 | Beaver |
| 5,593,619 A | 1/1997 | Bottelberghe et al. |
| 5,741,949 A | 4/1998 | Mack |
| 5,770,780 A | 6/1998 | Metz et al. |
| 5,831,137 A | 11/1998 | Metz et al. |
| 5,866,731 A | 2/1999 | Watanabe et al. |
| 5,866,732 A | 2/1999 | Eiermann et al. |

FOREIGN PATENT DOCUMENTS

| | | |
|---|---|---|
| DE | 1147574 | 4/1963 |
| EP | 0181414 A1 | 5/1986 |
| EP | 0429 059 A2 | 5/1991 |
| FR | 1.533.410 | 1/1969 |
| JP | 4[1992]-338344 | 11/1992 |

*Primary Examiner*—Alan Siegel
(74) *Attorney, Agent, or Firm*—E. E. Spielman, Jr.

(57) ABSTRACT

This invention relates to the production of an hexabromocyclododecane product, which process comprises brominating cyclododecatriene in the presence of a 1,4-dioxane and water based solvent and from about 0.5 to about 30 wt % bromide ion in the liquid phase of the reaction mass. Optional post-reaction heat treatment in a finishing step increases process yields if needed. The hexabromocyclododecane product is unrecrystallized and contains no more than about 1.5 wt % tetrabromocyclododecene impurities.

32 Claims, No Drawings

PROCESS FOR PRODUCING HEXABROMOCYCLODODECANE

REFERENCE TO RELATED APPLICATION

This is a Continuation of commonly-owned application Ser. No. 09/373,639, filed Aug. 18, 1999 now U.S. Pat. No. 6,284,935, which is a Continuation-in-Part of our prior application Ser. No. 09/353,181, filed Jul. 14, 1999, abandoned, which in turn is a Continuation-in-Part of prior application Ser. No. 09/253,874, filed Feb. 22, 1999, abandoned.

BACKGROUND OF THE INVENTION

This invention concerns an improved process for the production of hexabromocyclododecane. The process produces a low-melting, highly pure hexabromocyclododecane product.

Hexabromocyclododecane (1,2,5,6,9,10-hexabromocyclododecane) is a well established flame retardant for use in various thermoplastics. This compound is usually produced as a mix of its three stereoisomers, the alpha, beta and gamma isomers. It is preferred that the gamma isomer comprise about 70 wt % of the mix. Hexabromocyclododecane is commercially available as a product which contains principally hexabromocyclododecane and lesser amount of impurities. A principal impurity is the underbrominated species, tetrabromocyclododecene. The tetrabromocyclododecene impurities include the side-reaction products formed by the reaction of the brominating agent with cyclododecatriene, brominated cyclododecane and reactive solvents, e.g., alcohols.

The product is produced by the bromination of cyclododecatriene in the presence of a solvent, generally an alcohol, e.g., isobutanol. The alcohol can be used alone or in combination with a wide variety of co-solvents, e.g., halogenated hydrocarbons, dioxane, etc. The main drawbacks with using alcohol-based solvents are that (i) a significant amount of the reaction intermediate, tetrabromocyclododecene, precipitates out of the reaction solution before the intermediate has an opportunity to be hexabrominated, and (ii) alcohols readily react with the brominating reagent to produce undesirable side-reaction products and to consume brominating reagent. If the so-consumed brominating agent is not replaced, increased formation of underbrominated species, e.g., tetrabromocyclododecene, is likely to occur. The industry has responded to these drawbacks by suggesting that the reaction mass could be heated, in a finishing step, to redissolve the tetrabromocyclododecenes and then further brominating the tetrabromocyclododecenes to form the hexabromocyclododecane. However, heating of the reaction mass exacerbates the formation of undesirable side-reaction products derived from the solvent. To increase the purity of the finished hexabromo cyclododecane product, the crude process product is repeatedly washed with solvents, such as toluene, which will remove tetrabromocyclododecene and other impurities. Unfortunately, such washing will also remove significant amounts of the alpha and beta isomers which reduces the total yield of hexabromocyclododecane product. In addition, since the alpha and beta isomer content is reduced without a concomitant reduction in the gamma content, the melting point of the hexabromo cyclodecane product will be high, say between 185 to 200° C. Such high-melting products are commercially viable, however, the more commercially significant hexabromocyclododecane products are those having a melting point between 175 to 195° C., which products are referred to by the industry as low-melt products. Low-melt products generally contain 10 to 12 wt % alpha isomer, 4 to 9 wt % beta isomer and 71 to 78 wt % gamma isomer. But the problem with most low-melt products is that they have a high impurity content since they have not undergone the washing steps, indeed they contain up to about 10 wt % tetrabromocyclododecene. With a high impurity content, comes a less than desirable thermal stability.

It is an object of this invention to provide a process for the production of low-melt hexabromocyclododecane products having good thermal stability. This and other objects will be more fully understood from the following description of various processes and products which are claimed herein.

THE INVENTION

This invention provides a process which comprises brominating cyclododecatriene in a 1,4-dioxane and water solvent and in the presence of from about 0.5 to about 30 wt % bromide ion ($Br^{31}$), the wt % being based on the total weight of the liquid portion of the reaction mass.

Other embodiments, advantages, and features of this invention will be further apparent from the ensuing description and appended claims.

It has been discovered that by using a 1,4-dioxane-water solvent there is obtained, at reaction end, a reduction in the amount, i.e., to less than about 1.5 wt %, of tetrabromocyclododecene in the recovered hexabromocyclododecane product. (Unless otherwise stated, the wt % of the tetrabromocyclododecane, the isomers of hexabromocyclododecane, by-product impurities, etc., which are recited herein are all based on the total weight of the recovered hexabromocyclododecane product of which they are a constituent.) Also achieved is good utilization of the brominating agent, e.g., bromine. Both of these benefits are the result of the aqueous 1,4-dioxane being relatively inert in the reaction while having good solubility for tetrabromocyclododecenes at the reaction temperature, e.g., 20 to 50° C. By keeping most of the tetrabromocyclododecenes in solution during the reaction, it is more likely, over time and in some cases under heat, that the underbrominated species will be brominated to hexabromocyclododecane. Further, since aqueous 1,4-dioxane is relatively unreactive with the brominating agent, there are less by-product impurities formed and thus more brominating agent present in the reaction to promote the hexabromination of the tetrabromocyclododecenes. In addition, hexabromocyclododecane is relatively insoluble in the aqueous 1,4-dioxane solvents of this invention, thus very little is lost to the residual mother liquor after recovery of the precipitate. This, along with the perbromination of the tetrabromocyclododecene, promotes high yields.

While the aqueous 1,4-dioxane solvent system attenuates the formation of impurities and promotes the perbromination of tetrabromocyclododecene, this system does not produce a high gamma content. Generally, the gamma content will be about 50 wt %, the wt % being based on the total weight of brominated cyclododecatriene in the reaction mass. It has been discovered, however, that if the liquid portion of the reaction mass contains from about 0.5 to 30 wt %, and preferably from about 3 to about 30 wt %, bromide ion ($Br^-$), then the gamma content will be enhanced to 65 to 75 wt % on the same basis. Most preferred amounts of bromide ion are in the range of from about 4 to about 13 wt %. The wt % values for the bromide ion are based on the total weight of the liquid portion of the reaction mass. It is theorized, though this invention is not to be limited to any one theory, that the bromide ion complexes with the brominating agent, e.g., bromine, and that the resulting complex selectively assists bromination of the sterically hindered intermediates which leads to the gamma isomer. Thus, the formation of the gamma isomer is facilitated.

The process of this invention is similar to prior art processes in its operation and equipment used except for the aqueous 1,4-dioxane solvent system and the use of a high bromide ion content in the liquid portion of the reaction mass.

The brominating agent is preferably liquid bromine which is added as such to the reactor. It is within the scope of this invention, however, to produce the bromine in situ. For example, HBr can be fed to the reactor along with a oxidant such as $H_2O_2$ which will convert HBr to $Br_2$. Since HBr is a good source for the bromide ion feature of this invention, this mode of operation may be attractive as the HBr can be provided in an amount which fulfills both the $Br_2$ and the bromide ion needs. The $Br_2$ and HBr used should both be of good quality and essentially free of impurities. Commercially available grades of either of these two compounds are generally suitable.

The cyclododecatriene should also have a good quality and can be provided by most commercial grades of this compound. The usual molecular configuration of the cyclododecatriene corresponds to 1,5,9-cis,trans,trans-cyclododecatriene. However, the actual isomeric configuration of the cyclododecatriene is not deemed critical to the practice of this invention.

Quantitatively, the relationship between the amounts of cyclododecane and brominating agent is essentially stoichiometric to yield hexabromocyclododecane. Thus, if the brominating agent is $Br_2$, then three moles of $Br_2$ per mole of cyclododecatriene will be used. If, however, the brominating agent contains but a single Br constituent, then six moles per mole of cyclododecatriene will be used. The same 6:1 molar ratio applies if HBr is used to produce $Br_2$ in situ as discussed above. It is preferred to provide a small excess of brominating agent. Up to about 10% excess of stoichiometric is suitable, with about 2 to about 8% being preferred and about 2 to about 7% being most preferred. Amounts of brominating agent in excess of the just mentioned 10% may be used, but they are not preferred as they confer no significant benefit.

The aqueous 1,4-dioxane solvents of this invention most preferably contain no or very little alcohol or reactive species, say less than 5 wt %, and contain at least about 50 wt % 1,4-dioxane and no more than about 40 wt % water. Most preferred water and 1,4-dioxane solvents are those which contain up to about 40 wt % water and from about 99 to about 60 wt % 1,4-dioxane. Most preferably the 1,4-dioxane and water solvent will contain up to about 20 wt % water and from about 95 to about 80 wt % 1,4-dioxane. For the above described solvents, the weight percentages are based on the total weight of all of the components of the solvent system. The 1,4-dioxane component used in forming such mixed solvents is preferably of a commercial quality and more preferably it should be comprised of at least 95 wt % 1,4-dioxane. Most preferably, this solvent component should be comprised of 98+wt % 1,4-dioxane.

The weight ratio of solvent to total cyclododecatriene fed will generally be within the range of from about 30:1 to 2:1 and preferably within the range of from about 9:1 to about 3:1. Most preferred are those weight ratios within the range of from about 5:1 to about 4:1. The weight of the solvent is the total weight of the dioxane and water in the reaction mass.

It is not impermissible for the solvents of this invention to contain some alcohol or other reactive solvent species provided that the amount of such solvents does not deprive the process of the benefits from using a dioxane and water containing solvent. However, it is more preferred that the solvents of this invention be essentially free of alcohol or reactive species. By reactive species, it is meant species that are more reactive in the process than is dioxane.

The 1,4-dioxane and water solvents of this invention are, as noted above, relatively inert in the reaction. They do not exhibit the reactivity of prior art alcohol solvents. While the solvents of this invention are preferably essentially all, say 95+wt %, of a mix of 1,4-dioxane and water, it is to be understood that other solvent constituents, e.g., aliphatic ethers, esters, nitriles, nitroalkanes, aromatics and haloalkanes may be present, provided that their presence does not significantly denigrate the benefits obtained from the use of the 1,4-dioxane and water solvents. It is preferred that these other solvents comprise less than about 5 wt % of the total solvent, and most preferably less than about 1 wt % of the total solvent.

The bromide ion can be provided to the reaction mass by way of a bromide ion source which is soluble in the reaction mass under process conditions and which yields bromide ion under such conditions. Exemplary bromide ion sources are alkali metal bromide, alkaline earth metal bromide, organic bromide and mixtures of any two or more of the foregoing. Preferred are HBr, LiBr, NaBr or mixtures thereof. The HBr can be added directly to the reaction mass or can accompany the solvent system. For example, the solvent system can be produced from 1,4-dioxane and aqueous HBr or the solvent system can be a recycled mother liquor from a previously ran batch which contains HBr from prior direct additions and/or from in situ formation of HBr from the bromination of reaction mass species. If the bromide ion source is LiBr or NaBr, then it is simply added to the reaction mass. The particular identity of the bromide ion source is not critical to the process of this invention so long as it does not deleteriously affect the process and can effectively yield the desired level of bromide ion. The bromide ion can also be generated in situ via chemical or electrochemical action.

The processes of this invention are preferably practiced by first charging a reactor with the 1,4-dioxane and water solvent, and, optionally but preferably, bromide ion. To this initial charge is preferably added a pre-charge of brominating agent, which pre-charge will count against the total brominating agent used in the process. Cyclododecatriene and further brominating agent are then fed to the reactor. Throughout the cyclododecatriene and brominating agent feeds, the reaction mass is kept at a temperature between about 0° C. and about 80° C., and preferably below or equal to about 60° C. Most preferred temperatures are within the range of from about 20 to about 60° C. Most highly preferred are temperatures within the range of from about 20 to about 55° C. Temperatures much above about 80° C. will tend to retard the desired production of the gamma stereoisomer even in the presence of the bromide ion. The reaction pressure is not critical, with near atmospheric or atmospheric pressures being preferred.

When using the preferred practice of pre-charging a portion of the bromine to the reactor before the cyclododecatriene and main bromine feeds are initiated, the amount of the pre-charge is preferably within the range of from about 1 to about 10% of the total bromine used in the process. A more preferred pre-charge will be within the range of from about 2 to about 7% of the total bromine.

It is preferred that the cyclododecatriene and the brominating agent feeds occur at least partially at the same time.

It is most preferred that the periods of the two feeds be essentially, say 80+% of the time, simultaneous. Fully simultaneous feeds are highly preferred. The cyclododecatriene and brominating agent are preferably fed separately, simultaneously and from adjacent or spaced apart points of feed. Optionally, the brominating agent and/or cyclododecatriene may be fed into a circulating loop of reaction mixture instead of being fed directly into the reactor. For economical reasons it is preferred to simply inject the reagents into the reactor. While it is beneficial to have the cyclododecatriene and brominating feeds occur to together for at least some portion of the feed period, it is possible to pre-charge all of the bromine or cyclododecatriene to the reactor and to then add the other reagent over time. This latter feeding technique, while usable, is not preferred as it can result in reaction hot spots which can cause product quality and operational problems. In all cases, it is preferred that the brominating agent and cyclododecatriene be fed subsurface, say a few inches under the reaction mass surface, of the reaction mass in the reactor. The use of jet feeding for both reactants is preferred as it contributes to their facile and quick mixing. Any jet velocity that assists in providing the amount of mixing desired, e.g., on the order of about 0.3 to about 10 ft/sec, can be used. In all cases the reactor should provide stirring, the overall object being the thorough mixing of the reactor contents.

After the cyclododecatriene and bromine feeds are finished, the reaction mass typically will be a slurry containing hexabromocyclododecane (precipitate and solute), 1,4-dioxane and water solvent, bromide ion, unreacted bromine and partially brominated cyclododecatrienes (precipitate and solute), the latter being predominately tetrabromocyclododecenes, say from about 5 to about 15 wt % (the wt % being based on the total amount of brominated cyclododecatriene present in the reaction mass at that time). Most of the partially brominated cyclododecatrienes are solutes in the liquid phase of the reaction mass. The solid phase of the reaction mass is an easily recovered hexabromocyclododecane product precipitate which contains the earlier-mentioned low amounts of the tetrabromocyclododecenes.

It may be desirable, depending upon the economics of any particular process of this invention, for the practitioner to convert at least a part of the underbrominated cyclododecatriene to hexabromocyclododecane. Simple heating of the reaction mass will convert a significant amount of the tetrabromocyclododecene solutes in the reaction mass to hexabromocyclododecane which will almost all go towards the formation of the hexabromocyclododecane product precipitate. The heating step is without significant down-side in the processes of this invention as the inert 1,4-dioxane and water solvent does not react with reaction mass constituents which is unlike the situation which occurs when the solvent contains a reactive species, such as an alcohol. Thus, an advantage for the solvents of this invention is that a highly pure product containing no or little solvent derived by-products and little or no tetrabromocyclododecenes can be obtained directly without the need for further purification steps, e.g., recrystallization, which is indicated for systems using a reactive solvent such as alcohol.

The thermal finishing step is preferably performed without a work-up of the reaction mass. It is convenient to simply leave the reaction mass, as is, in the reaction vessel and to then apply heat for the desired period of time. Suitable reaction mass temperatures are within the range of from about 70 to about 90° C., and preferably within the range of from about 70 to about 80° C. The reaction mass is maintained at the elevated temperature for a period of time so that the desired amount of tetrabromocyclododecenes are converted to hexabromocyclododecane. Generally, the heat-treatment temperature is maintained for a period of from about 1 to about 120 minutes, and preferably from about 1 to about 60 minutes. The shorter times are useful when the tetrabromocyclododecene content of the reaction mass is low, the longer times being useful when the tetrabromocyclododecene content is higher. The use of a heat treatment step is indicated if the process without heat treatment does not provide the desired low level of tetrabromocyclododecene in the recovered hexabromocyclododecane product.

Depending upon the cost allocable to heating of the reaction mass for the finishing step versus the cost of process time, it could be desirable to simply let the reaction mass come to about ambient temperature and sit for an extended period of time to await conversion of residual tetrabromocyclododecenes to hexabromocyclododecane. This technique will not be economically favored in most cases.

After the thermal finishing step or after the brominating agent and cyclododecatriene feeds are completed, if no finishing step is used, the reaction mass is preferably allowed to cool to about ambient temperature. The liquid phase and the solid phase of the reaction mass are then conventionally separated, e.g., by centrifugation, decantation or filtration. A final hexabromocyclododecane product can be obtained by simply water washing the separated solid phase, i.e., the precipitated hexabromocyclododecane product. It is preferred, however, to wash the precipitated hexabromocyclododecane product with 1,4-dioxane or a mixture of 1,4-dioxane and water. Preferably, the precipitated hexabromocyclododecane product is washed with a mixture of 1,4-dioxane and water in which from 50 to 100 wt % is 1,4-dioxane with the balance being water. If needed to remove acidic components from the precipitate, e.g., HBr, the precipitate can be washed to at least near neutrality with a dilute base, say aqueous ammonium hydroxide. After all washing has been accomplished, the washed precipitate is oven dried at a temperature within the range of from about 90 to about 115° C.

Hexabromocyclododecane product yields can be increased by recycling the mother liquor, the wash liquor and their respective unfiltered solids to subsequent reactions.

The processes of this invention can be run in the batch, semi-continuous or continuous modes.

The finished hexabromocyclododecane products of this invention have no recrystallization history, i.e., they have not been redissolved and recrystallized for the purpose of purification. Preferred hexabromocyclododecane products of this invention have a content of hexabromocyclododecane alpha isomer that is no higher than about 25 wt %, a content of hexabromocyclododecane beta isomer that is no higher than about 20 wt %, a hexabromocyclododecane gamma isomer content that is no lower than about 65 wt %, and a tetrabromocyclododecene content, if any, that is no higher than about 2 wt %, and most preferably no higher than about 1.5 wt %. Particularly desirable hexabromocyclododecane products of this invention have an hexabromocyclododecane alpha isomer content in the range of from about 10 to about 20 wt %, (preferably from about 14 to about 19 wt %), a hexabromocyclododecane beta isomer content in the range of from about 7 to about 16 wt %,(preferably from about 10 to about 13 wt %) a hexabromocyclododecane gamma isomer content in the range of from about 65 to about 80 wt %, (preferably from about 65 to about 75 wt %) and a tetrabromocyclododecene content, if any, of no more than about 1.5 wt % and preferably less than 1.0 wt %. Most preferred tetrabromocyclododecene contents are below about 0.5 wt % and most highly preferred within the range of from about 0.01 to about 0.4 wt %. In this connection, all analytical determinations of product composition (as weight percentages) referred to in this document utilized the following procedure: The ratio of the hexabromocyclododecane isomers and detection of tetrabromocyclododecene impurities were determined by high pressure liquid chromatography. The sample is prepared in tetrahydrofuran/ acetonitrile solvent at a concentration of 10 mg/mL. The dilute solution is injected onto a Zorbax ODS 4.6 mm×250 mm column maintained at 20° C. The eluent is acetonitrile/ water, 80/20, v/v at a flow rate of 1 mL/min. Detection was made by a Hitachi L-4000 UV detector at 220 nm. Recording and integration were accomplished by a Hewlett Packard 3396A integrator. The response factor of all components were assumed to be equal. The retention times of the three hexabromocyclododecane isomers are: alpha(12.1 min.), beta (13.6 min.), and gamma (19.3 min.). The value for the tetrabromocyclododecene isomers is the sum of the peak areas between 13.6 to 19.3 min.

The hexabromocyclododecane products produced by the process of this invention have an initial differential scanning calorimetric (DSC) melting point of 165 to 180° C. and a final melting point of about 175 to 200° C. Preferred initial melting points are in the range from 170 to 180° C. (Hexabromocyclododecane products, because they are a mix of stereoisomers and impurities, do not exhibit sharp melting points but rather have melting points which extend over a fairly broad range in the order of about 10 to 30 degrees centigrade. This phenomenon is well recognized in the art.) DSC melt points were obtained on a Mettler TC-11 Controller with DCS-25. 10 mg of product is weighed accurately into a 40 microliter aluminum crucible with lid. The conditions of the instrument are as follows: start temperature— 120° C., temperature rate—2° C./min, final temperature— 210° C. The initial melt point is calculated by drawing a tangent from the inflection point on the front of the melt point curve to the extrapolated baseline.

The hexabromocyclododecane products of this invention exhibit excellent thermal stability while still containing significant amounts of the alpha and beta isomers. The hexabromocyclododecane products of this invention evolve HBr upon heating to a much lesser extent than do other hexabromocyclododecane products with similar isomer composition ratios. For example, a hexabromocyclododecane product obtained from a conventional process using a alcohol based solvent system evolved>1000 ppm HBr upon heating at 160° C. for 30 minutes. A hexabromocyclododecane product of this invention, under the same test conditions, evolved less than 400 ppm HBr. Preferred hexabromocyclododecane products of this invention will less than 100 ppm HBr. HBr evolution is measured by heating a sample of the product, capturing the off gases evolved during the heating and titrating the captured gases to determine their HBr content.

More particularly, a 2.00±0.01 g sample is first weighed in a 20×150 mm tared test tube. Three 250 mL sidearm filter flasks are filled with 150–170 mL of 0.1N NaOH (enough to completely cover the frit) containing phenolphthalein (2% w/v solution in 3A EtOH), and are connected one with the other in series with Viton® tubing. The first flask is then connected to the flask. This allows the acidic gases generated by the heated sample in the test tube to be passed through the aqueous NaOH, thus trapping the HBr. The test tube containing the sample is fitted with a No. 2 neoprene stopper with a 1/16" inlet and a 7 mm outlet for Teflon® tubing. The sample in the test tube is purged with nitrogen (flow rate=0.5 SCFH) for five minutes. The test tube is then placed in a silicon oil bath (160° C.) deep enough to surround the entire sample for 30 minutes. The sample containing test tube is withdrawn from the bath and purged with nitrogen for another five minutes. The test tube containing the pyrolysed sample is removed and replaced with a clean empty test tube. This test tube is placed under nitrogen purge and is submerged in the salt bath for five minutes to flush out any residual HBr.

After this last purge the test tube is rinsed and all lines are rinsed with deionized (di) $H_2O$, keeping nitrogen flow through the test tube during the rinse. The rinsing begins with the last collection flask and works back to the first. The rinsing liquids are added to the flasks. The contents of the flasks are then combined and quantitatively transferred to bottles followed by rinsing with di $H_2O$.

The bottled contents are sampled and the samples titrated using a Metrohm 716 titroprocessor with an Ag combination electrode. Each sample is acidified with a 1:2 solution of $HNO_3$; DI $H_2O$, to a pH<7 and then titrated with standardized $AgNO_3$ to a potentiometric equivalence point. The parameters for the titration are those which are recommended in the manual for the titroprocessor. Variations of those parameters are left to the discretion of the operator. The results are reported in duplicate as ppm HBr.

Calculations $$\text{ppm HBr}=(Epl \text{ mL}*\text{Nitrant}*\text{molecular wt. HBr}*1,000,000)/(\text{wt. of Sample}*1000)$$

where

Ep=endpoint volume in mL and

Nitrant =Normality of $AgNO_3$

The hexabromocyclododecane products of this invention are suitable for use as flame retardants in thermoplastic formulations. They are useful, for example, in high impact polystyrene, expanded polystyrene, extruded polystyrene, polypropylene and epoxy thermosets. The products are also useful in textiles, paints and hot melts. In the foregoing applications, conventional loadings are useful and conventional additives, such as synergists, antioxidants, pigments, fillers, acid scavengers and UV stabilizers may also be used in conventional amounts. Preferred loadings for the hexabromocyclododecane products of this invention are within the range of from about 0.8 to about 3 wt %, the wt % being based upon the total weight of the thermoplastic formulation.

The following Examples, wherein all parts and percentages are by weight unless specified otherwise, are illustrative of the processes this invention. The Examples are not intended to limit, and should not be construed as limiting, the scope of the invention.

EXAMPLE I

A 5 L multi-neck, fully-jacketed round bottom flask was charged with 3130 g of neat 1,4-dioxane and 870 g of aqueous 60% HBr (6.44 mol HBr). Cyclododecatriene (CDT) (630 g, 3.89 mol, 5.5:1 loading) and bromine (1959 g, 12.24 mol, 5% mol excess) were primed for subsurface co-feed. Bromine (90 g, 0.56 mol) was pre-charged to the reactor before beginning the CDT feed. Feed rates for the CDT and bromine were adjusted so that both feeds ended simultaneously after 105 minutes. A cooling system was used to insure that the reaction temperature did not exceed 40° C. during the feeding period. At feed completion, it was determined that a thermal finishing step would be suitable. Thus, hot glycol was circulated to warm the reaction mass to approximately 90° C. where it was maintained for approximately 120 minutes. After this period the reaction mass was allowed to cool to ambient temperature. The reaction mass was centrifuged in six drops, with each drop being washed with 300 g of a 90 wt % 1,4-dioxane in water mix. The combined solids from each drop were then slurried in two portions each in 2 liters 0.05% ammonium hydroxide. Vacuum filtration, and washing with water was followed by oven drying overnight at 95° C. gave a white hexabromocyclododecane product (1765 g, 70% yield). The yield was based on the moles of hexabromocyclododecane product recovered per mole of cyclododecatriene used in the reaction.

The following Table gives an analysis of the hexabromocyclododecane product produced by the procedure of Example I. The Table also gives an analysis of a hexabromocyclododecane product produced conventionally using isobutyl alcohol as the process solvent.

TABLE

| HBCD Product Analysis | HBCD Product from Example | HBCD Product from Isobutyl Alcohol Process |
|---|---|---|
| alpha | 16.3 wt % | 13.1 wt % |
| beta | 12.3 wt % | 6.1 wt % |
| tetra | 0.2 wt % | 4.7 wt % |
| gamma | 71.1 wt % | 75.5 wt % |
| total HBCD* | 99.7 wt % | 94.9 wt % |
| melt point** | 181–194 | 181–195 |

*Total hBCD is the amount of hexabromocyclododecane in the hexabromocyclododecane product
**Visual Melt point is measured as ° C.

EXAMPLE II

The procedure of Example I is repeated except for the following changes: (1) the vessel is a 5 L baffled reaction kettle, (2) the source of the HBr is aqueous 48% HBr, (3) the feeds occur over 20–30 minutes through 1/32 inch orifices, (4) the reaction slurry is heated at approximately 70° C. for 10 minutes, (5) the centrifuged solids are washed with a 50:50 wt % mixture of 1,4-dioxane and water, and (6) the solid is slurried in hot aqueous ammonium hydroxide. The isolated material was equivalent quality to that from Example I.

EXAMPLE III

A batch of hexabromocyclododecane was produced by mixing 10.2 parts of mother liquor, 1 part of cyclododecatriene, and 3 parts of bromine. The mother liquor had made two previous batches of hexabromocyclododecane and was used without any treatment. The mother liquor consisted of 11.9 parts of dioxane, 1.5 parts of water, and 1 part of hydrogen bromide. The bromine was in 2 mol % excess based on cyclododecatriene and the entire excess was added to the reaction mixture before the feeds were begun. The cyclododecatriene and bromine were simultaneously fed subsurface, each through a small orifice to obtain a jetting action, into the agitated reaction mixture. The temperature was maintained at or below 40° C. for the entire reaction. After cooling, the batch was isolated via centrifugation and washed with 90% aqueous dioxane (solid:wash, 1:0.9, wt:wt). The solid was then reslurried in water (solid:water, 1:1.7, wt:wt) again centrifuged and washed with hot water (solid:wash, 1:1.6, wt:wt). The solid was oven dried at 115° C. to yield 3.52 parts of white hexabromocyclododecane in 88% yield based on cyclododecatriene. The solid's visual melting point was 178–196° C., and the solid consisted of isomers alpha (13.5%), beta (9.3%), gamma (75.7%), and tetrabromocyclododecenes (<0.5%).

EXAMPLE IV

A 1 L multi-neck, fully-jacketed round bottom flask was charged with 700 g of mother liquor from a prior batch. The mother liquor consisted of 27 parts of dioxane, 2.7 parts of water, 1.7 parts of hydrogen bromide, and 1 part of bromine. Cyclododecatriene (CDT) (64.8 g) and bromine (191.9 g) were primed for subsurface co-feed. The reactor charge was warmed to 45° C., cooled to 35° C., and then maintained at 40° C. during the reaction. Feed rates for the CDT and bromine were adjusted so that both feeds ended simultaneously after 140 minutes. Composition of the reaction mass was similar to the previous examples.

This invention is susceptible to considerable variation in its practice. Therefore, the foregoing description is not intended to limit, and should not be construed as limiting, the invention to the particular exemplifications presented hereinabove. Rather, what is intended to be covered is as set forth in the ensuing claims and the equivalents thereof permitted as a matter of law.

What is claimed is:

1. A process for the production of hexabromocyclododecane, which process comprises: simultaneously feeding a brominating agent and cyclododecatriene to a reaction mass containing (i) a solvent comprised of 1,4-dioxane and water and (ii) from about 0.5 to about 30 wt % bromide ion, the wt % being based on the total weight of the liquid portion of the reaction.

2. The process of claim 1 wherein the simultaneous feeding occurs at least 80% of the total feed times for each feed.

3. The process of claim 1 wherein the simultaneous feeding is fully simultaneous for the total feed times for each feed.

4. The process of claim 1 wherein there is feeding of brominating agent and cyclodoecatriene sub-surface of the reaction mass.

5. The process of claim 4 wherein the sub-surface feed is effected by jet feeding.

6. The process of claim 5 wherein the jet feeding provides a jet velocity for each feed of from about 0.3 to about 10 ft/sec.

7. The process of claim 1 wherein the brominating agent is bromine.

8. The process of claim 1 wherein the brominating agent is HBr and wherein there is provided $H_2O_2$ for oxidizing HBr to bromine.

9. The process of claim 1 wherein a portion of the brominating agent is HBr and wherein there is provided $H_2O_2$ for oxidizing HBr to bromine.

10. The process of claim 1 wherein the solvent contains no more than about 40 wt % water, the wt % being based on the total weight of the solvent.

11. The process of claim 1 wherein the solvent contains up to about 20 wt % water and from about 80 to about 95 wt % dioxane.

12. The process of claim 1 wherein the reaction mass is pre-charged with bromine before the bromine and cyclododecatriene feeds are initiated.

13. The process of claim 12 wherein the pre-charge of bromine is within the range of from about 1 to about 10% of the total bromine used in the process.

14. The process of claim 12 wherein the pre-charge of bromine is within the range of from about 2 to about 7% of the total bromine used in the process.

15. The process of claim 12 wherein the solvent contains no more than about 40 wt % water, the wt % being based on the total weight of the solvent.

16. The process of claim 13 wherein the solvent contains up to about 20 wt % water and from about 80 to about 95 wt % dioxane.

17. A process for the production of hexabromocyclododecane, which process comprises: simultaneously feeding a brominating agent and cyclododecatriene to a reaction mass containing a solvent having less than 5 wt % alcohol or reactive species and which is comprised of 1,4-dioxane and water.

18. The process of claim 17 wherein the simultaneous feeding occurs at least 80% of the total feed times for each feed.

19. The process of claim 17 wherein the simultaneous feeding is fully simultaneous for the total feed times for each feed.

20. The process of claim 17 wherein there is feeding of brominating agent and cyclodoecatriene sub-surface of the reaction mass.

21. The process of claim 20 wherein the sub-surface feed is effected by jet feeding.

22. The process of claim 21 wherein the jet feeding provides a jet velocity for each feed of from about 0.3 to about 10 ft/sec.

23. The process of claim 17 wherein the brominating agent is bromine.

24. The process of claim 17 wherein the brominating agent is HBr and wherein there is provided $H_2O_2$ for oxidizing HBr to bromine.

25. The process of claim 17 wherein a portion of the brominating agent is HBr and wherein there is provided $H_2O_2$ for oxidizing HBr to bromine.

26. The process of claim 17 wherein the solvent contains no more than about 40 wt % water, the wt % being based on the total weight of the solvent.

27. The process of claim 17 wherein the solvent contains up to about 20 wt % water and from about 80 to about 95 wt % dioxane.

28. The process of claim 17 wherein the reaction mass is pre-charged with bromine before the bromine and cyclododecatriene feeds are initiated.

29. The process of claim 28 wherein the pre-charge of bromine is within the range of from about 1 to about 10% of the total bromine used in the process.

30. The process of claim 28 wherein the pre-charge of bromine is within the range of from about 2 to about 7% of the total bromine used in the process.

31. The process of claim 28 wherein the solvent contains no more than about 40 wt % water, the wt % being based on the total weight of the solvent.

32. The process of claim 29 wherein the solvent contains up to about 20 wt % water and from about 80 to about 95 wt % dioxane.

* * * * *